United States Patent

Obara et al.

[11] 3,932,538
[45] Jan. 13, 1976

[54] PROCESS FOR PRODUCING PYROGALLOL AND DERIVATIVES THEREOF

[75] Inventors: Heitaro Obara; Junichi Onodera, both of Yonezawa; Akira Matukuma, Tokyo; Kenji Yoshida, Yokohama, all of Japan

[73] Assignee: Mitsubishi Chemical Industries, Limited, Tokyo, Japan

[22] Filed: Sept. 30, 1974

[21] Appl. No.: 510,754

[30] Foreign Application Priority Data
Sept. 29, 1973  Japan............................. 48-109977

[52] U.S. Cl............................ 260/625; 260/621 M
[51] Int. Cl.².................................. C07C 39/10
[58] Field of Search....................... 260/621 M, 625

[56] References Cited
UNITED STATES PATENTS

| | | | |
|---|---|---|---|
| 2,273,030 | 2/1942 | Fitzky et al. | 260/621 |
| 2,289,001 | 7/1942 | Fitzky et al. | 260/621 |
| 3,462,497 | 8/1969 | Greco | 260/621 |
| 3,530,186 | 9/1970 | Greco | 260/571 |

FOREIGN PATENTS OR APPLICATIONS
1,195,327   6/1965   Germany

*Primary Examiner*—James O. Thomas, Jr.
*Assistant Examiner*—W. B. Lone
*Attorney, Agent, or Firm*—Oblon, Fisher, Spivak, McClelland & Maier

[57] ABSTRACT

A process for producing pyrogallol or 5-substituted pyrogallol having the formula:

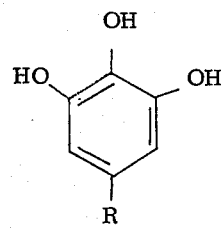

wherein R is selected from the group consisting of alkyl, cycloalkyl, aryl, and aralkyl, or a mixture thereof which comprises heating an aqueous solution of 4-substituted-2,6-diaminophenol or 4-substituted-2,6-diamino 1-alkoxybenzene having the formula:

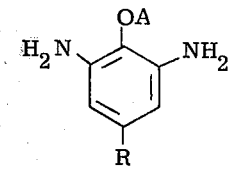

wherein R is as defined above and A is selected from the group consisting of hydrogen and alkyl, under acid conditions.

10 Claims, No Drawings

PROCESS FOR PRODUCING PYROGALLOL AND DERIVATIVES THEREOF

BACKGROUND OF THE INVENTION

1. Field of the Invention

The present invention relates to the process for producing pyrogallol and 5-substituted pyrogallol.

2. Description of the Prior Art

Pyrogallol has been produced conventionally by decarboxylation of gallic acid (3,4,5-trihydroxybenzoic acid) by heating an aqueous solution of gallic acid at elevated temperatures under high pressures. However, the primary source of gallic acid is gall extracts and therefore the availability of gallic acid is quite limited and the costs are quite high.

Another known process for the production of pyrogallol is hydroxylation of catechol or resorcinol with hydrogen peroxide. This technique, however, has been found to be generally unsuitable for technical production. Accordingly, the range of usefulness of pyrogallol has been heretofore limited to applications such as an intermediate for certain pharmaceuticals, an analytical reagent or a reagent for absorption of oxygen, which requires only relatively small quantities of pyrogallol.

A need exists, therefore, for a method of producing pyrogallol and 5-substituted pyrogallol on an industrial scale whereby the costs of production would be drastically cut, thereby permitting these compounds to be used more widely, particularly in the field of agricultural chemicals, pharmaceuticals, dyestuffs and the like.

SUMMARY OF THE INVENTION

Accordingly, one object of the present invention is to provide a process for producing pyrogallol and 5-substituted pyrogallol in high yields and at relatively low cost.

This and other objects of this invention, as will hereinafter become better understood by the following description, have been attained in this invention by providing a method for producing pyrogallol or 5-substituted pyrogallol from petrochemical products.

According to this method, 5-substituted pyrogallol having the formula I

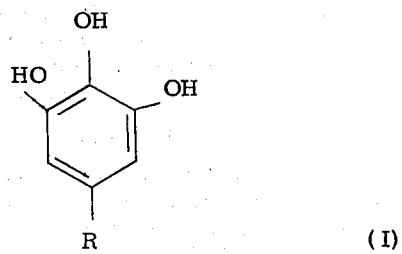

(I)

wherein R is selected from the group consisting of alkyl, cycloalkyl, aryl and aralkyl, and/or pyrogallol is produced by heating an aqueous solution of 4-substituted-2,6-diaminophenol or 4-substituted-2,6-diamino-1-alkoxybenzene having the formula II:

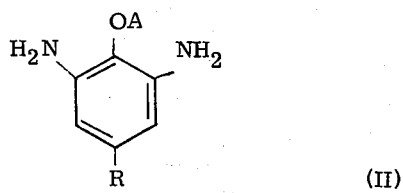

(II)

wherein R is the same as in the formula I, and A is selected from the group consisting of hydrogen and alkyl, under acid conditions.

DETAILED DESCRIPTION OF PREFERRED EMBODIMENTS

The reactants used in the invention are 4-substituted-2,6-diamino-phenol and 4-substituted-2,6-diamino-1-alkoxybenzene, represented by the formula II, wherein R is selected from the group consisting of alkyl, cycloalkyl, aryl, and aralkyl, such as methyl, ethyl, n-propyl, isopropyl, sec-butyl, tert-butyl, 1-methylbutyl, 1-ethyl-1,1-dimethylbutyl, 1,3-dimethylbutyl, 1,1,3,3-tetramethylbutyl, cyclopentyl, cyclohexyl, 1-methylcyclopentyl, 1-methylcyclohexyl, phenyl, benzyl, 1-phenylethyl, 1-methyl-1-(3,5-diamino-4-hydroxyphenyl)ethyl and the like. Preferred are alkyl, cycloalkyl, aralkyl, or those containing lower alkyl groups of 1 – 10 carbon atoms.

Pyrogallol and/or 5-substituted pyrogallol can be obtained in good yields only when 4-substituted-2,6-diaminophenol is used. The 4-substituent seems to provide a certain degree of stability which is essential to the reaction. When 4-unsubstituted-2,6-diaminophenol is hydrolyzed, the yields are quite poor. Also, hydrolysis of 4-substituted-2,6-diaminophenol or 4-substituted-2,6-diamino-1-alkoxybenzene in which the 4-substituent is carboxyl or alkoxy carbonyl groups, provides poor yields.

The reaction is carried out by heating said 4-substituted-2,6-diaminophenol or 4-substituted-2,6-diaminophenol or 4-substituted-2,6-diamino-1-alkoxy benzene to a temperature of 150° – 300°C, preferably 200° – 270°C in an acidic aqueous solution. The concentration of 4-substituted-2,6-diaminophenol or 4-substituted-2,6-diamino-1-alkoxybenzene should be no more than 20 wt %, preferably 0.5–12 wt %. If it is over 20 wt %, the yield will apparently decrease, because of the resinification. On the other hand, too low a concentration will be economically disadvantageous.

The 4-substituted-2,6 diaminophenol or 4-substituted-2,6-diamino-1-alkoxybenzene is readily converted in accordance with the present invention by heating to an elevated temperature in the presence of an acid substance. Examples of suitable acids are hydrochloric acid, hydrobromic acid, sulfuric acid, phosphoric acid, methanesulfonic acid, and the like. Hydrochloric acid is preferably used.

The acid can be normally employed in about an equivalent amount required for neutralization of 4-substituted-2,6-diaminophenol or 4-substituted-2,6-diamino-1-alkoxybenzene. Addition of any excess amount of acid would result in the decreased yields.

The resinification of the product is prevented and the yield thereby enhanced, if the reaction is carried out in the inert gas atmosphere. Approximately 1–20 kg/cm² of an inert gas, for example, hydrogen, nitrogen, carbon dioxide, helium, argon or the like is introduced in addition to the vapor pressure of water formed by heating. The heating time will vary widely depending upon the particular reaction temperature, and generally ranges from 1 to 20 hours.

If the reaction is carried out at elevated temperatures employing 2,6-diaminophenol or 2,6-diamino-1- alkoxybenzene, substituted at the 4th position by an alkyl group, a cycloalkyl group or an aralkyl group respectively having tertiary carbon atom at the 1st position (bonded directly to the benzene ring), the substituent is eliminated simultaneously with the hydrolysis of amino groups, and the desired pyrogallol is obtained.

Namely pyrogallol is easily obtained by heating to a temperature above 200°C, preferably 220°–270°C for 2–20 hours, which effects the nearly complete elimination of the alkyl group, cycloalkyl group or aralkyl group, respectively having tertiary carbon atoms at the 1st position (bonded directly to the benzene ring).

The 5-substituted pyrogallol is obtained nearly selectively by heating 2,6-diaminophenol or 2,6-diamino-1-alkoxybenzene substituted at the 4th position by an alkyl group, a cycloalkyl group, an aryl group or an aralkyl group, respectively, having a primary or a secondary carbon atom at the 1st position (bonded directly to the benzene ring), to the above defined reaction temperature.

After completion of the reaction, the reaction mixture is evaporated to dryness, and the residue is extracted with a solvent such as methanol, acetone, ethyl acetate or the like. The extract obtained thereby is separated into its components by distillation.

Having generally described the invention, a further understanding can be obtained by certain specific examples which are provided herein for purposes of illustration only and are not intended to be limiting in any manner.

EXAMPLE 1

Into 10 l Ti autoclave, 177.2 g of 2,6-diamino-4-tert-butyl-phenol dihydrochloride and 2978 g of water was placed, and air was replaced with nitrogen gas of 10 kg/cm² pressure. The reaction vessel was heated to 250°C for 8 hours. After the reaction was completed, the aqueous solution was evaporated to dryness. The mixture of organic substance and ammonium chloride, thus obtained, was analyzed by gas chromatography after trimethylsilylation. Thus the yields were determined from chromatograph as 39.2% pyrogallol and 6.5% 5-tert-butylpyrogallol. The reaction product was extracted with methanol, and the extract was distilled at first at atmospheric pressure to remove the methanol, then distilled in vacus. The fraction boiling at 147°–152°C/5mmHg, was identified as pyrogallol, m.p. 130°–132°C. The fraction, boiling at 150°–156°C/3mmHg, was identified as 5-tert-butylpyrogallol, m.p. 133°–135°C. Elemental analysis for $C_{10}H_{14}O_3$: calcd., C 79.95, H 9.40%; obsd., C 79.26, H 9.28%.

EXAMPLE 2

The procedure of Example 1 is repeated to study the effects of reaction conditions, such as concentration of 2,6-diamino-4-tertbutyl phenol, reaction temperature, reaction time, effect of particular sealing gas, and effect of different acids on the yield of pyrogallol and 5-tert-butylpyrogallol. The results are shown in Table 1. In this Table 1, the concentration shows the weight (g) of free 2,6-diamino-4-tert-butylphenol in 100 g of water. The quantity of reaction medium was 80 ml, and the reaction was carried out in a 200 cc autoclave.

TABLE 1

| Run No. | Concn | Reaction Conditions |  |  |  | Yield (%) |  |
|---|---|---|---|---|---|---|---|
| | | Temp. (°C) | Time (hr) | Sealed gas | Acid | Pyrogallol (%) | 5-tert-butyl-pyrogallol (%) |
| 1 | 8.7 | 250 | 8 | N₂ | HCl | 31.0 | 6.3 |
| 2 | 6.4 | '' | '' | '' | '' | 34.3 | 8.3 |
| 3 | 4.2 | '' | '' | '' | '' | 38.6 | 9.7 |
| 4 | 1.0 | '' | '' | '' | '' | 47.8 | 8.6 |
| 5 | 0.5 | '' | '' | '' | '' | 44.5 | 20.8 |
| 6 | 0.2 | '' | '' | '' | '' | 37.2 | 29.7 |
| 7 | 4.2 | '' | 2 | '' | '' | 14.2 | 39.0 |
| 8 | '' | '' | 16 | '' | '' | 39.3 | 7.0 |
| 9 | '' | 200 | 72 | '' | '' | 26.5 | 31.1 |
| 10 | '' | '' | 16 | '' | '' | 0.9 | 9.0 |
| 11 | '' | 265 | 4 | '' | '' | 31.8 | 4.2 |
| 12 | '' | '' | 1 | '' | '' | 22.6 | 8.7 |
| 13 | '' | 250 | 4 | H₂ | '' | 42.1 | 2.9 |
| 14 | '' | '' | 8 | none | '' | 35.5 | 1.6 |
| 15 | '' | '' | '' | H₂ | HBr | 38.2 | 9.3 |
| 16 | '' | '' | '' | '' | H₂SO₄ | 34.5 | 8.2 |
| 17 | '' | '' | '' | '' | H₃PO₄ | 35.9 | 10.4 |

EXAMPLE 3

The procedure of Example 1 is repeated except that 2,6-diamino-4-methyl-phenol dihydrochloride was used as the starting material. 295.5 g of 2,6-diamino-4-methylphenol dihydrochloride was dissolved in 4541 g of water, and the solution was placed into a 10 liter Ti autoclave, then heated to 250°C for 8 hours. After similar treatment as described in Example 1, 5-methyl-pyrogallol, m.p. 124.5°–125°C, was obtained in 37.1% yield. Elemental analysis for $C_7H_8O_3$: Calculated: C 60.00, H 5.75%; Observed: C 60.14, H 5.85%. Pyrogallol was not recognized in the reaction product.

EXAMPLE 4

The procedure of Example 1 is repeated except 2,6-diamino-4-sec.-butylphenol dihydrochloride was used as the starting material. 354.4 g of 2,6-diamino-4-sec.-butyl phenol dihydrochloride was dissolved in 5954 g of water, and the solution was placed into a 10 liter Ti autoclave, then heated to 250°C for 8 hours. After similar treatment as described in Example 1, 5-sec.-butylpyrogallol, m.p. 89.5°–90.5°C, b.p. 145°C/3 mmHg, was obtained in 37.8% yield. Elemental analysis for $C_{10}H_{14}O_3$: Calculated: C 79.95, H 9.40%; Observed: C 78.89, H 9.20%. Pyrogallol was also recognized in 3.1% yield.

EXAMPLE 5

The procedure of Example 1 was repeated except 2,6-diamino-4-tert-butylanisole dihydrochloride was used as the starting material. 0.802 g of 2,6-diamino-4- tert-butylanisole dihydrochloride was dissolved in 12.72 g of water, and the solution was placed in a Pyrex glass ampoule, sealing with 1 atm. nitrogen gas, then heated to 250°C for 8 hours. After the reaction was completed, the solution was analyzed and the yield was determined. Thus 24.1% pyrogallol and 8.3% 5-tert-butylpyrogallol was obtained, but 2,6-dihydroxyanisole or 2,6-dihydroxy-4-tert-butylanisole was not recognized.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for producing pyrogallol, which comprises: heating an aqueous solution of 4-substituted-2,6-diamino-phenol or 4-substituted-2,6-diamino-1-alkoxy benzene having the formula:

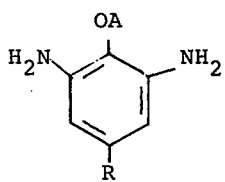

wherein R is alkyl, cycloalkyl, or aralkyl, respectively, having from 1 to 10 carbon atoms and having a tertiary carbon atom bonded directly to the nuclear benzene carbon atom, and A is hydrogen or alkyl, having from 1 to 10 carbon atoms at a temperature of 150°–300°C in the presence of hydrochloric acid, hydrobromic acid, sulfuric acid, phosphoric acid, methane sulfonic acid or trifluoromethane sulfonic acid.

2. The process according to claim 1 wherein R is selected from the group consisting of tertiary-butyl 1,1-dimethylbutyl 1,1,3,3-tetramethylbutyl, 1-methylcyclopentyl, and 1-methyl-1-(3,5-diamino-4-hydroxyphenyl)ethyl, and A is selected from the group consisting of hydrogen, methyl and ethyl.

3. The process according to claim 1, wherein said 4-substituted-2,6-diaminophenol is 2,6-diamino-4-tert-butylphenol.

4. The process according to claim 1, wherein said 4-substituted-2,6-diamino-1-alkoxybenzene is 2,6-diamino-4-tert-butylanisole.

5. The process according to claim 1, wherein said aqueous solution contains 0.5–12 wt% of 4-substituted-2,6-diaminophenol or 4-substituted-2,6-diamino-1-alkoxybenzene.

6. The process according to claim 1, wherein said aqueous solution of 4-substituted-2,6-diaminophenol or 4-substituted-2,6-diamino-1-alkoxy-benzene is heated to a temperature of 200°–270°C for 1–20 hours.

7. The process according to claim 1, wherein an acid is used in approximately an amount required for neutralization of 4-substituted-2,6-diaminophenol or 4-substituted-2,6-diamino-1-alkoxybenzene.

8. The process according to claim 1, wherein said aqueous solution of 4-substituted-2,6-diamino-1-alkoxybenzene is heated under the atmosphere of an inert gas selected from the group consisting of hydrogen, nitrogen, carbon dioxide, helium and argon.

9. The process according to claim 8, wherein the pressure of an inert gas is 1–20 kg/cm².

10. A process for producing pyrogallol, which comprises: heating an aqueous solution containing 0.5 – 12 wt% of 4-substituted-2,6-diaminophenol or 4-substituted-2,6-diamino-1-alkoxybenzene having the formula:

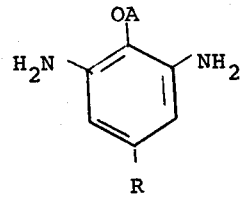

wherein R is alkyl, cycloalkyl, or aralkyl, respectively, having from 1–10 carbon atoms and having a tertiary carbon atom which is bonded directly to the nuclear benzene carbon atom, and A is hydrogen or alkyl having not more than 10 carbon atoms, at a temperature of 150°–300°C in the presence of hydrochloric acid, hydrobromic acid, sulfuric acid, phosphoric acid, methane sulfonic acid or trifluoromethane sulfonic acid under an atmosphere of an inert gas selected from the group consisting of hydrogen, nitrogen, carbon dioxide, helium, and argon, for a time sufficient to effect substantial conversion thereof.

* * * * *